(12) United States Patent
Roby et al.

(10) Patent No.: US 9,937,063 B2
(45) Date of Patent: Apr. 10, 2018

(54) TRIALING FOR PROSTHETIC COMPONENT

(71) Applicant: Zimmer, Inc., Warsaw, IN (US)

(72) Inventors: Keith A. Roby, Jersey City, NJ (US);
Greg Stebbins, Hoboken, NJ (US);
Jorge Montoya, Madison, NJ (US);
Ray Zubok, Midland Park, NJ (US)

(73) Assignee: Zimmer, Inc., Warsaw, IN (US)

( * ) Notice: Subject to any disclaimer, the term of this patent is extended or adjusted under 35 U.S.C. 154(b) by 1093 days.

(21) Appl. No.: 14/180,950

(22) Filed: Feb. 14, 2014

(65) Prior Publication Data
US 2014/0228846 A1 Aug. 14, 2014

Related U.S. Application Data

(60) Provisional application No. 61/764,838, filed on Feb. 14, 2013.

(51) Int. Cl.
*A61B 17/00* (2006.01)
*A61F 2/46* (2006.01)
(Continued)

(52) U.S. Cl.
CPC ........ *A61F 2/4684* (2013.01); *A61B 17/1659* (2013.01); *A61B 17/1675* (2013.01); *A61F 2/389* (2013.01)

(58) Field of Classification Search
CPC .......... A61F 2/46; A61F 2/4684; A61F 2/389; A61B 17/1659; A61B 17/1675
See application file for complete search history.

(56) References Cited

U.S. PATENT DOCUMENTS 5,514,143 A * 5/1996 Bonutti ............... A61B 17/154
606/79
5,976,147 A 11/1999 LaSalle et al.
(Continued)

FOREIGN PATENT DOCUMENTS

EP 1415625 A2 5/2004
WO WO-2014127229 A1 8/2014

OTHER PUBLICATIONS

"International Application Serial No. PCT/US2014/016468, International Search Report dated Apr. 22, 2014", 6 pgs.
(Continued)

*Primary Examiner* — Alvin Stewart
(74) *Attorney, Agent, or Firm* — Schwegman Lundberg & Woessner, P.A.

(57) ABSTRACT

An orthopedic system according to one embodiment of the disclosure comprises a first trial member capable of forming a broach cavity in a first bone of a patient. A second trial member is removeably coupleable to the first trial member in a fixed alignment with respect to the trial member. An alignment member is removeably coupleable in a fixed alignment with respect to the first trial member. The alignment member comprises indicia configured to provide for alignment of the alignment member with respect to at least one of the first bone and a second bone of the patient. The alignment of the second trial member with respect to the first trial member when coupled to the first trial member corresponds to the alignment of the alignment member with respect to the first trial member when coupled with the first trial member.

20 Claims, 11 Drawing Sheets

(51) Int. Cl.
*A61B 17/16* (2006.01)
*A61F 2/38* (2006.01)

(56) References Cited

U.S. PATENT DOCUMENTS

| | | | | |
|---|---|---|---|---|
| 6,159,216 | A * | 12/2000 | Burkinshaw | A61B 17/1735 606/88 |
| 6,355,045 | B1 * | 3/2002 | Gundlapalli | A61B 17/1764 606/86 R |
| 8,968,412 | B2 * | 3/2015 | Wogoman | A61F 2/4684 623/20.15 |
| 2005/0075640 | A1 * | 4/2005 | Collazo | A61B 17/1764 606/86 R |
| 2006/0184176 | A1 * | 8/2006 | Straszheim-Morley | A61B 17/1764 606/88 |
| 2012/0158152 | A1 * | 6/2012 | Claypool | A61F 2/389 623/20.33 |
| 2013/0006253 | A1 * | 1/2013 | Waite, II | A61B 17/1675 606/88 |
| 2013/0006370 | A1 * | 1/2013 | Wogoman | A61F 2/4684 623/20.16 |
| 2013/0030538 | A1 * | 1/2013 | Metzger | A61B 17/025 623/20.3 |
| 2013/0261505 | A1 * | 10/2013 | Sherman | A61F 2/4657 600/595 |
| 2013/0261759 | A1 * | 10/2013 | Claypool | A61F 2/4657 623/20.33 |
| 2014/0172112 | A1 * | 6/2014 | Marter | A61F 2/4684 623/20.32 |
| 2014/0228846 | A1 * | 8/2014 | Roby | A61B 17/1659 606/79 |

OTHER PUBLICATIONS

"International Application Serial No. PCT/US2014/016468, Written Opinion dated Apr. 22, 2014", 7 pgs.

"International Application Serial No. PCT/US2014/016468, International Preliminary Report on Patentability dated Aug. 27, 2015", 9 pgs.

* cited by examiner

TRIALING FOR PROSTHETIC COMPONENT

CLAIM OF PRIORITY

This application claims the benefit of U.S. Provisional Patent Application Ser. No. 61/764,838, filed on Feb. 14, 2013, the benefit of priority of which is claimed hereby, and which is incorporated by reference herein in its entirety.

BACKGROUND

One or more trial components may be used by a surgeon or other medical practitioner during orthopedic surgery. A trial component generally refers to a temporary component that a surgeon locates in a patient to determine an acceptable geometry for a permanent implant component, e.g., with a trial component having features (e.g., size and shape) that substantially match those of a corresponding permanent implant. For example, a surgeon may position at least one trial component in a patient to check the compatibility of a particular geometry with the patient's anatomy or with respect to another system component.

For a total knee arthroplasty (TKA) surgery, also known as total knee replacement (TKR) surgery, a trial tibial component can include a trial base plate and a stem that extends from the base plate for insertion into the medullary canal of the tibia. A trial system can also include any number of other components such as one or more augment trials or provisionals. The trial stem and base plate simulate a stem and base plate that eventually will be permanently implanted in the patient. Other trial components, such as a trial femoral stem and a trial condyl portion of a trial femoral component, can also be used in TKA surgery. In addition to knee surgeries, many other types of orthopedic surgeries can utilize one or more trial components to determine an acceptable geometry for an eventual permanent implant.

When implanting an orthopedic device in bone, such as in the proximal region of a tibia, it may be necessary to clear pre-existing matter in a specific or predetermined size. This may be accomplished, for example, by using a broach, drill or reamer. Illustratively, during the TKA surgery described above, when a guide within the tibial medullary canal is introduced, the proximal tibia may be broached over the guide to provide an opening of a desired size for a trial augment or provisional.

SUMMARY

The present disclosure, in certain embodiments, relates to trial systems for implantable orthopedic devices, such as joint replacement devices, for example an artificial knee. An illustrative trial system includes a combination broach and trial member that is capable of broaching a bone of a patient and an alignment member that provides for alignment of the trial member with respect to a part of the patient's anatomy, such as a first bone that the trial member is to be inserted into or another bone that is in close proximity to the first bone. In one example, the combination broach and trial member used with the alignment member may be implemented during a total knee arthroplasty (TKA) surgery, for example as part of a trial version of the tibial component of the knee implant.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure relates generally to components that may be used as trials for an implantable orthopedic implant, such as a joint replacement implant, for example an artificial knee. A "trial component," as it is used herein, generally refers to a temporary component that is introduced into a patient so that a surgeon or other medical professional can determine a geometry that is acceptable for the patient for a component or components of the orthopedic implant. Generally, the trial component or components simulate corresponding permanent components that will be implanted into the patient, e.g., with each trial component having a geometry (e.g., size and shape) that substantially matches the geometry of a corresponding permanent component. A surgeon or other medical practitioner may place at least one trial component into a patient in order to check the compatibility of a particular geometry with a patient's anatomy or with respect to another system component.

In order to demonstrate the concepts of the present disclosure, an example of an orthopedic implant comprising an artificial knee implant that can be used in a total knee arthroplasty (TKA) surgery will be described. The present disclosure is not limited to an artificial knee implant, however. The concepts of the present disclosure can be applied to any type of orthopedic implant trial system such as those used in conjunction with prosthetic hip, ankle, foot, shoulder, elbow and wrist implant systems or with any other type of joint or bone prosthesis.

Figure 1:
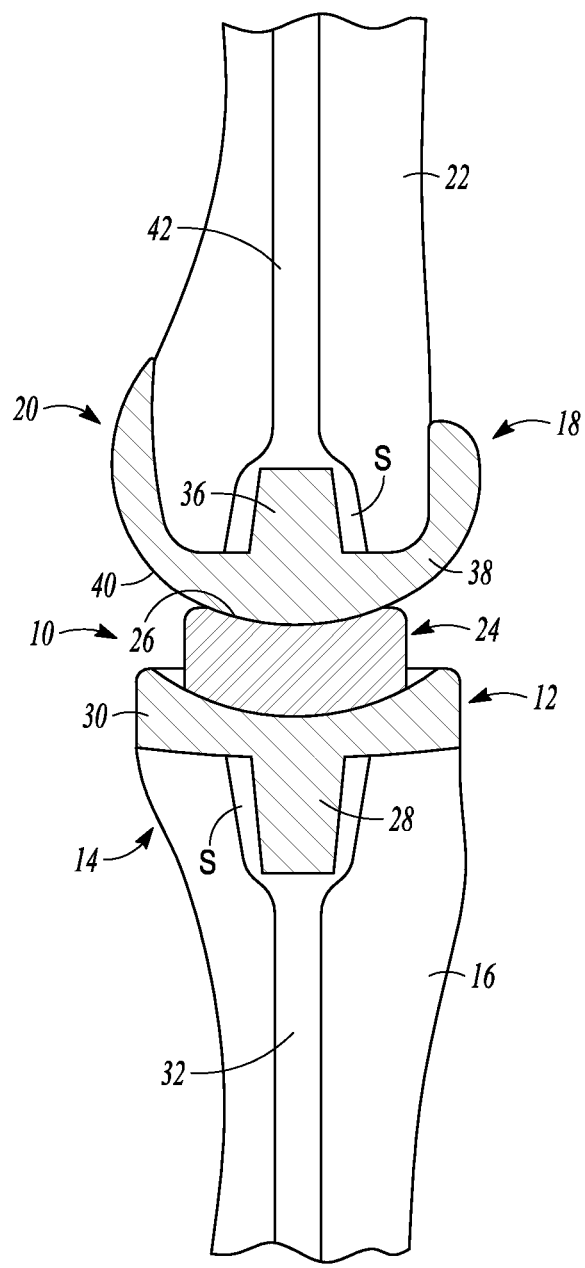
FIG. 1 is a cross-sectional view of an example artificial knee implant implanted in a patient after a total knee arthroplasty surgery.

FIG. 1 shows an example of an artificial knee implant 10 that may be implanted as part of a TKA surgery on a patient. The TKA surgery may include the use of a trial system comprising one or more trial components that simulate the permanent components of artificial knee implant 10, as described in more detail below. In an example, the artificial knee 10 comprises a tibial component 12 coupled to a proximal end 14 of the tibia 16, a femoral component 18 coupled to a distal end 20 of the femur 22, and an articulation component 24 between the tibial component 12 and the femoral component 18 to provide a low-friction articulation surface 26 for sliding motion between the tibial component 12 and the femoral component 18.

As shown in FIG. 1, in an example, the tibial component 12 comprises a stem 28 and a base plate 30, also sometimes referred to as a tibial platform 30. The stem 28 can be implanted into the tibia 16, for example, extending into the medullary canal 32 of the tibia 16. The stem 28 can provide a surface or surfaces for coupling or attachment between the tibial component 12 and the tibia 16. Although not shown, a stem extension will typically be coupled to the stem 28 for extending further into the medullary canal 32. The base plate 30 can provide support for the articulation component 24, such as within a cup or depression 34 within the base plate 30.

In an example, the femoral component 18 comprises a stem 36 and at least one condyle portion 38 comprising at least one generally convexly-curved condyle surface 40. The stem 36 can be implanted into the femur 22, for example, extending into the medullary canal 42 of the femur 22. The stem 36 can provide a surface or surfaces for coupling or attachment between the femoral component 18 and the femur 22. Although not shown, a stem extension will typically be coupled to the stem 36 for extending further into the medullary canal 42. The condyle surface 40 can interact with the articulation surface 26 in order to provide a sliding relationship between the femoral component 18 and the articulation component 24, and in turn with the tibial component 12 in order to simulate a natural knee joint.

The position or alignment of the components of the artificial knee 10 with respect to one another, such as the position or alignment of the tibial component 12 with respect to the tibia 16, the position or alignment of the tibial component 12 with respect to the articulation component 24, the position or alignment of the tibial component 12 with respect to the femoral component 18, the position or alignment of the femoral component 18 with respect to the articulation component 24, and/or the position or alignment of the femoral component 18 with respect to the femur 22, can affect the operation of the artificial knee 10, such as the patient's comfort or range of motion. Therefore, a surgeon or other medical practitioner will often use trial components that simulate one or more components of the artificial knee 10 in order to determine a geometry of the knee implant that provides for acceptable range of motion for the particular patient. For example, a trial tibial component can be coupled with the tibia 16, a trial femoral component can be coupled with the femur 22, and a trial articulation component can be positioned between the trial tibial component and the trial femoral component.

For some patients, there may be bone loss or damage to the bone or bones to which the components of an orthopedic implant are to be coupled. For example, it is often the case that for a TKA surgery, the tibia 16 or the femur 22 may have significant bone loss. If such damage or bone loss is present in a sufficient amount, a component of an orthopedic implant that is to be coupled to the damaged or diminished bone can comprise an augmentation structure that fills or supports missing, damaged or removed bone. Such structures can exhibit any suitable size and shape. Suitable shapes include but are not limited to generally cylindrical and conical shapes. In some instances, the augmentation structure will provide a porous or highly porous infrastructure, e.g., including a surface formed with a porous material or being formed entirely with a porous material such as a highly porous metallic material, for encouraging bone ingrowth into the augmentation structure to enhance the securement of the orthopedic implant component to the bone. For example, for TKA surgery, damage or bone loss in the proximal tibia can be augmented with a structure, such as an augmentation cone, that is inserted into the tibia (into an opening 66 in the proximal tibia as shown in FIG. 3). In the example shown in FIG. 1, a frustoconcial or other suitably shaped body (not shown) can be received around the stem 28 of the tibial component 12 to occupy a space "S" and provide an augmentation structure, for example, where the stem is received in a passage that extends entirely or partially through the augmentation body and is fixedly attached to inner walls of the passage. In some forms, the augmentation structure will have a cross section that is slightly larger than at least a portion of the tibial medullary canal 32. In the example of FIG. 1, such an augmentation structure can be coupled to the platform or base plate 30 of the tibial component 12.

Figure 2:
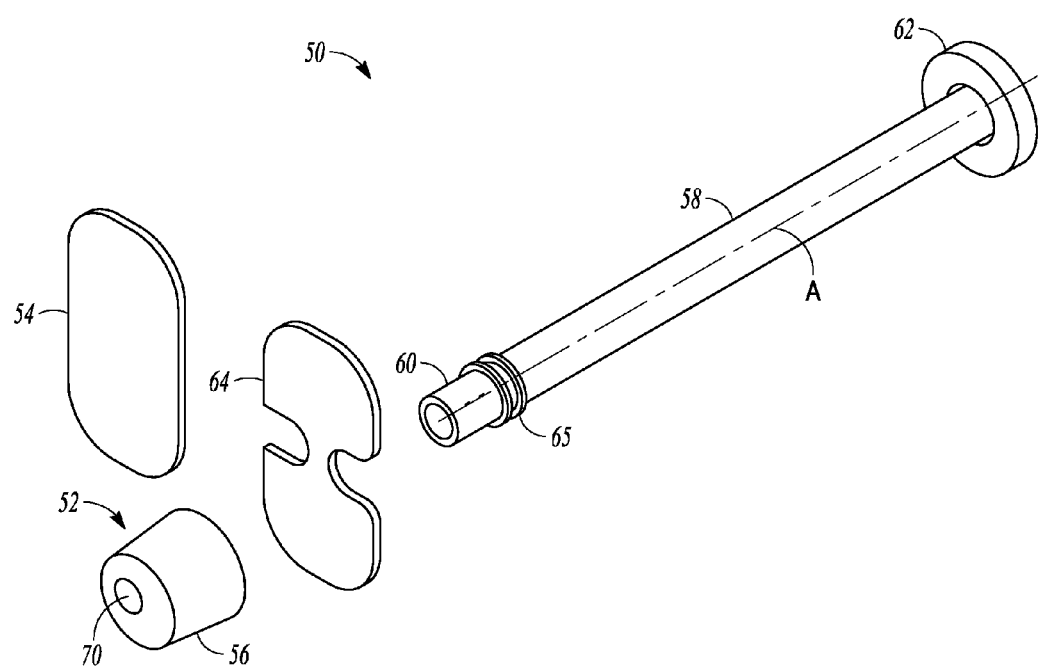
FIG. 2 is a perspective view of an example trial system that can provide for a trial fit of a tibial component of an artificial knee implant.

FIG. 2 shows an example of a trial system 50 that can be used to simulate one or more components of an orthopedic implant, such as the artificial knee 10 described above. In some instances, a permanent tibial component such as that shown in FIG. 1 will comprise an augmentation structure, such as a conical augment positioned around stem 28 as discussed above. In this regard, the trial system 50 can include one or more trial members 52, 54 that each act to substantially mimic the physical features of components of a permanent orthopedic implant. For example, the trial member 52 can simulate an augment cone positioned around the stem 28 of the tibial component 12 of the artificial knee 10 described above, and the trial member 54 can simulate the permanent base plate 30 of the tibial component 12. For this reason, the trial member 52 will also be referred to herein as the trial cone 52, and the trial member 54 will also be referred to herein as the trial base plate 54. While not necessary to broader aspects of the disclosure, as discussed in greater detail below, the trial cone 52 in this particular instance has a frustoconical shape with a cylindrical bore 70 extending through the cone in an eccentric manner. The central longitudinal axis of the bore 70 is offset somewhat from the central longitudinal axis of the trial cone 52 which in this instance happens to be a right cylindrical cone.

The size of an augmentation structure, such as an augmentation cone to be positioned around stem 28, is often but not necessarily larger in at least one direction than an opening in the bone into which the augmentation structure is to be placed, such as an opening in the tibial medullary canal 32. In order to place the trial cone 52 into the bone, an opening of generally the same size and shape as the trial cone is formed in the bone, often referred to as broaching the bone. The trial system 50 of the present disclosure includes a trial cone 52 that is also capable of forming a broach cavity in a bone of the patient so that a surgeon or other medical professional can simply broach the bone and leave the broaching cone 52 in the bone, rather than having a tool to broach the bone that is separate from the trial cone. The combination broach and trial cone 52 of the present disclosure simplifies the surgical procedure by combining two steps (e.g., broaching and placement of the trial cone 52) into a single step. In an example, an outer surface 56 of trial cone 52 has a generally frustoconical shape in order to simulate a generally frustoconical shape of the permanent augmentation cone to be positioned around stem 28. Such an outer surface is configured to facilitate broaching into the bone of the patient, for example by forming a broach cavity in the bone, such as with knurling or other surface features (not shown) that allow for broaching of the bone as the trial cone 52 is driven into the bone, as described in more detail below.

In an example, the trial cone 52 can be removably coupled to a handle 58 that provides for easy manipulation of the trial cone 52, particularly during broaching. The handle 58 can comprise an attachment structure 60 for detachably coupling the handle 58 to the trial cone 52. The trial cone 52 can comprise a corresponding attachment structure (not shown) that mates or otherwise interacts with the handle attachment structure 60 to provide a detachable coupling. The detachable coupling between the handle 58 and the trial cone 52 allows the handle 58 to be decoupled from the trial cone 52 after broaching the bone and installing the trial cone in the bone has been completed. Detachable coupling of the handle to the trial cone 52 can be achieved using any suitable coupling arrangement including but not limited to any number of screw-type systems, push-button quick release systems, taper lock systems, snap fit systems, and other suitable systems for detachably coupling one member to another.

In an example, the handle 58 comprises an impactor head 62 that provides a target impact surface for an impactor tool, such as a hammer. A surgeon or other medical practitioner can strike the impactor head 62 with the impactor tool in order to drive the trial cone 52 into the bone and broach the bone. The surgeon or other medical practitioner can strike the impactor head 62 any suitable number of times.

Continuing with FIG. 2, the example trial system 50 can also include a means for aligning the trial cone 52 with respect to a part of the patient's anatomy, such as the bone that the trial cone is to be inserted into, e.g., the tibia 16, and/or another bone of the patient, such as the femur 22, and/or for aligning the trial cone 52 with respect to a second trial member such as trial base plate 54. For example, if the trial system 50 is meant to simulate the tibial component 12 of the artificial knee implant 10, then the means for aligning the trial cone 52 can provide for alignment of the trial cone 52 with respect to the patient's tibia 16, with respect to the patient's femur 22, with respect to a position or alignment of the trial base plate 54, or with respect to a position or location of a trial femoral component (not shown). By providing for alignment of the trial cone 52, the means for aligning the trial cone 52 can also provide for a desired alignment of any component that may later be directly or indirectly coupled to the trial cone 52, such as a trial base plate of a tibial component for an artificial knee implant. In an example, shown in FIG. 2, the means for aligning the trial cone 52 comprises an alignment member 64 that is removably coupleable with the handle 58. In some preferred forms, this coupling arrangement substantially places the alignment member 64 in a rotationally fixed relationship with respect to the trial cone 52 about a common axis so that when the alignment member 64 is rotated by a particular amount, e.g., by a particular rotational angle, the trial cone 52 is rotated by a substantially identical amount. For designs in which the alignment member is coupleable with the handle, optionally, the alignment member can be disengaged from the handle to allow an acceptable degree of misalignment between the two. In an example, the trial cone 52 and the alignment member 64 can both be coupled, either directly or indirectly, to the handle 58 in a manner such that both the trial cone 52 and the alignment member 64 will rotate about a longitudinal axis A of the handle 58 in a rotationally fixed relationship with respect to each other. In the example shown in FIG. 2, the alignment member 64 can be coupled to the handle 58 via an attachment member 65, such as a pair of ridges on the handle 58 that the alignment member 64 can fit between, e.g., forming an interference fit, in order to provide for a rotationally fixed relationship between the alignment member 64 and the handle 58. In another example (not shown), the alignment member 64 can be coupled to the trial cone 52, either as an alternative to, or in addition to, being coupled to the handle, for example, using the same connecting structure that can couple the trial cone 52 to the trial base plate 54 (described below). In such instances, the trial cone 52 and/or the alignment member 64 can then be coupled to the handle 58.

The alignment member 64 can comprise indicia that are configured to provide for the alignment of the alignment member 64 or the trial cone 52 with respect to at least one of the bone the trial cone 52 is being implanted in (e.g., the tibia 16), a second bone that may be proximate to the bone the trial cone 52 is being implanted in (such as the femur 22), and/or another system component such as the trial base plate 54 or a trial femoral component (not shown). In an example, the indicia can comprise features of a shape of the alignment member 64 that can be positioned relative to a landmark on a bone or another trial component by a surgeon or other medical practitioner. In some forms, alignment member 64 will include windows 67 (e.g., as shown in FIG. 3B below) or other openings therein, for example, to allow a surgeon or other practitioner to see through the member to view portions of the trial cone 52 and/or nearby anatomical features to assist in a broaching and/or alignment step. A number of other view-enhancing features are contemplated as well. Illustratively, the alignment member 64, or any portion thereof, could exhibit some degree of transparency.

In an example where the trial cone 52 simulates a conical augment to be positioned around a stem of an artificial knee implant like implant 10, the alignment member 64 can have a shape that is substantially similar to a shape of the trial base plate 54 that will be coupled to the trial cone 52, as shown in FIG. 2. In such a case, a surgeon or other medical practitioner can position the alignment member 64 in an orientation or position that corresponds to an acceptable final orientation or position of the trial base plate 54. The surgeon or other medical practitioner can then decouple the alignment member 64 from the trial cone 52 and then couple the trial base plate 54 to the trial cone 52 in substantially the same orientation or position that was vacated by the alignment member 64.

In an example, the means for aligning the trial cone 52 can comprise indicia located on the trial cone 52 that can be used to align the trial cone 52 with a feature of the bone into which the trial cone 52 is being broached or another bone proximate to the bone into which the trial cone 52 is being broached. For example, for a trial cone 52 that simulates a conical augment to be positioned around a stem of a tibial component such as tibial component 12, the trial cone 52 may be configured with indicia, such as a pointer or laser mark that is formed on the trial cone 52, that can be aligned with a bone feature of the tibia 16, such as a specific point on a condyle to be positioned near the proximal end 14 of the tibia 16. A surgeon or other medical practitioner can ensure that the indicia remains aligned with the bone feature of interest until broaching with the trial cone 52 is complete such that the trial cone 52 remains in a desired alignment during essentially the entirety of the broaching of the bone with the trial cone 52. Viewing of such indicia can be facilitated by certain structural features of the alignment member 64 such as windows 67 as shown in FIG. 3B.

Figure 3A:
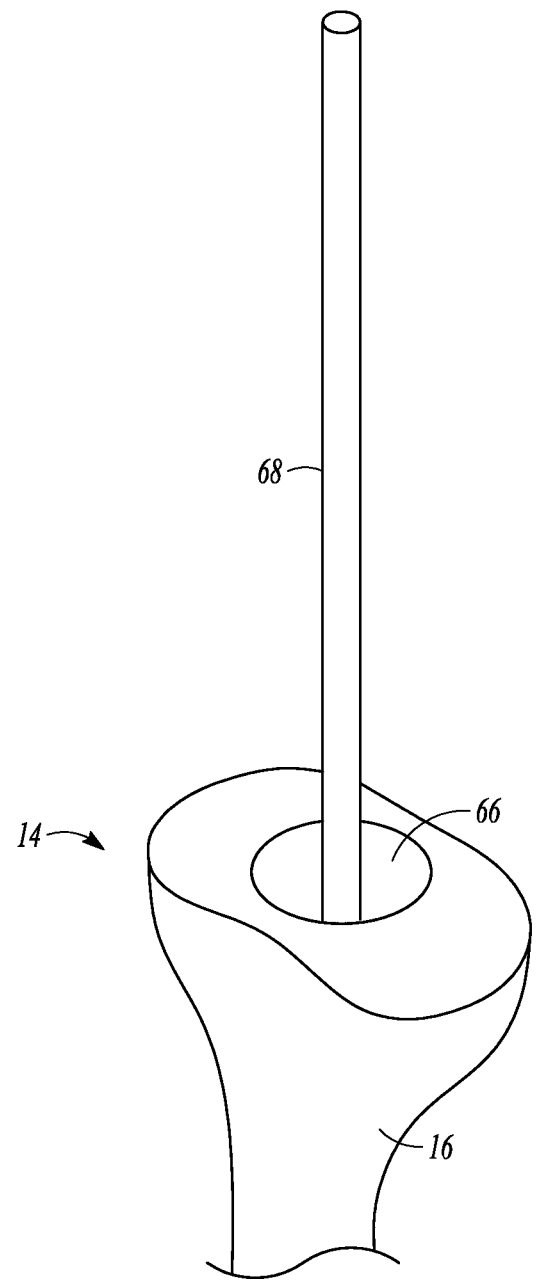
FIGS. 3A-3D show a perspective view of various stages of an example method of installing the example trial system of FIG. 2 onto the tibia of a patient.
Figure 3B:
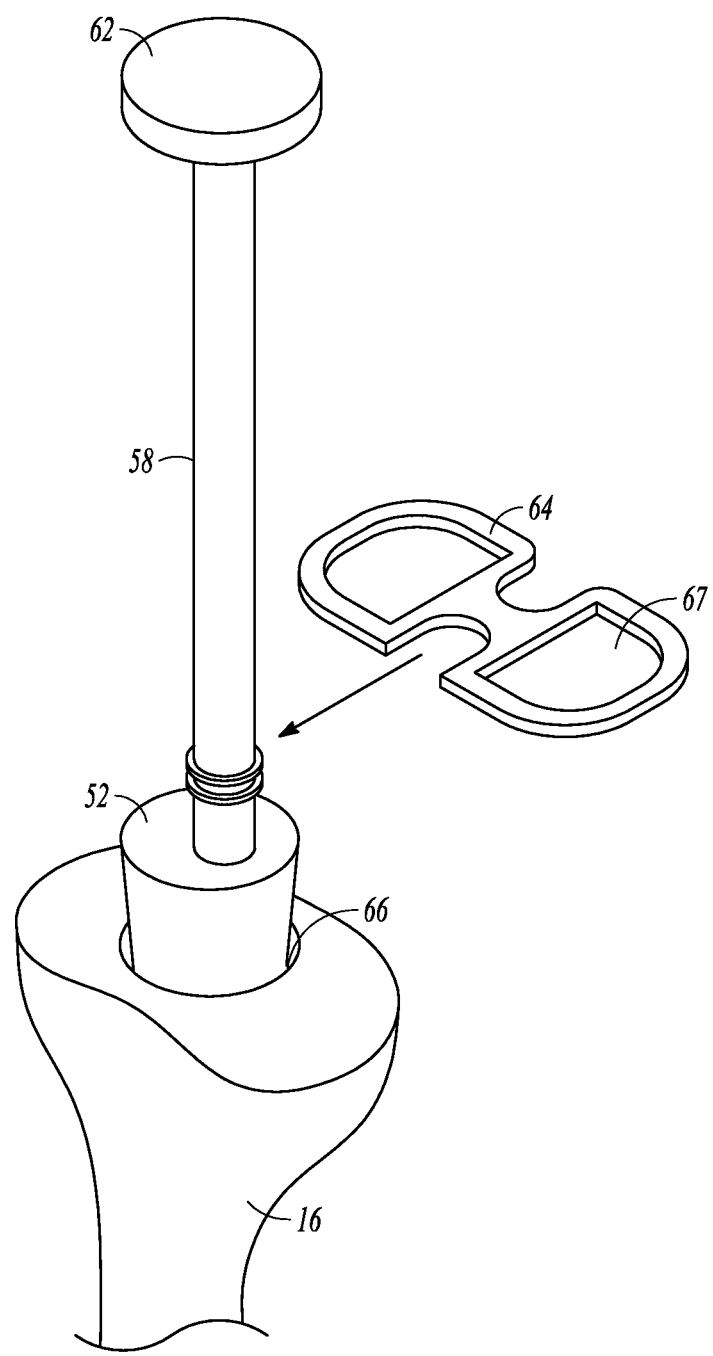
Figure 3C:
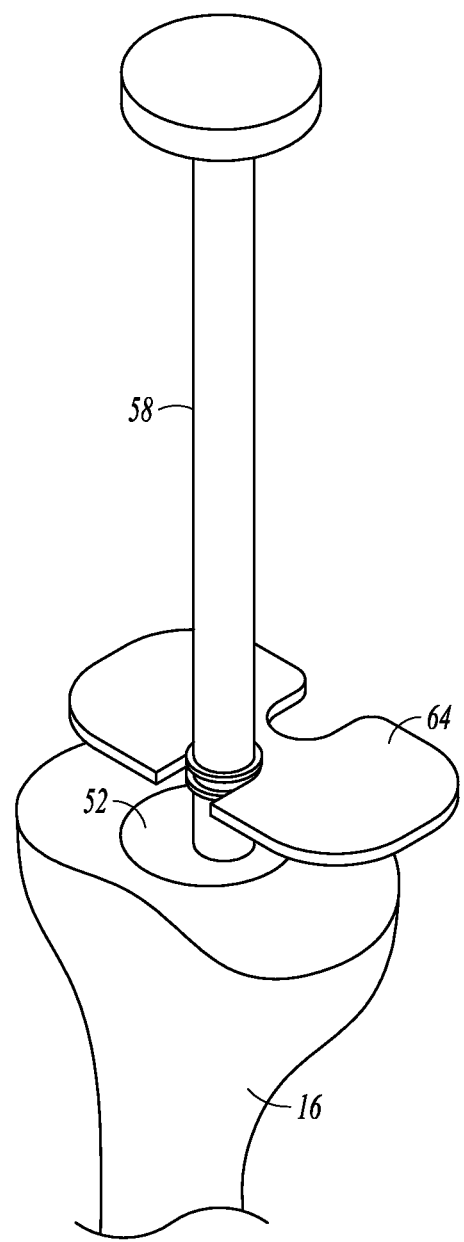
Figure 3D:
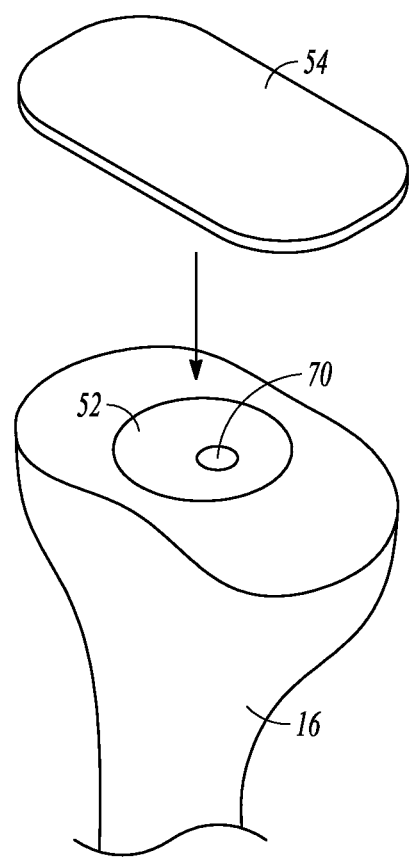
Figure 4A:
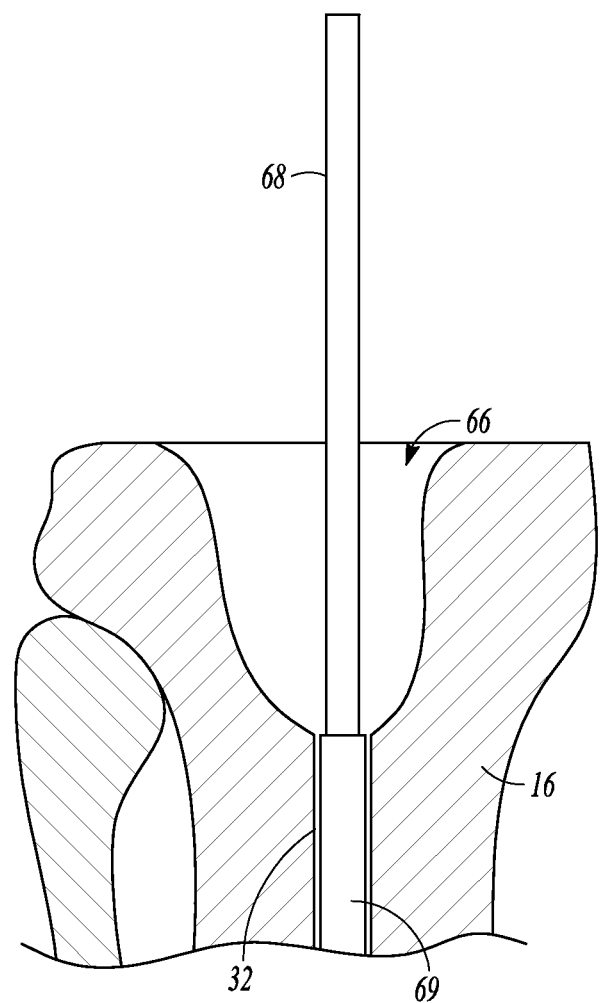
FIGS. 4A-4D show a cross-sectional side view of various stages of an example method of installing the example trial system of FIG. 2 onto the tibia of a patient.

FIGS. 3A-3D and FIGS. 4A-4D shows several steps of an example method of using a trial system 50, with FIGS. 3A-3D showing a perspective view and FIGS. 4A-4D showing a cross-sectional side view at several points during the method. FIGS. 3A and 4A show the proximal end 14 of tibia 16 after a portion of the proximal end 14 has been resected, such as by cutting through the tibia 16 with a bone saw to expose an opening 66 in the proximal tibia, e.g., into the medullary canal 32. A stem extension provisional 69 (not visible in FIG. 3A) is connected to an alignment rod 68, and this combination has been placed through the opening 66 to provide a mechanism for properly aligning the trial cone 52 within the opening 66 (e.g., as shown in FIG. 3B). A number of additional steps will have been carried out before the stem extension provisional and alignment rod combination are inserted in the tibia. For example, after the tibia is resected, a sizing plate (not shown) will typically be pinned to the resected bone, and a drill will be advanced through an opening in the sizing plate to create space in the medullary canal for the trial stem extension 69. It is typically around this time that the surgeon decides whether one or more augment structures should be employed in the final implant system, and if so, what should be the shapes and sizes of any such structures. For example, in some instances upon resecting the proximal tibia as shown in FIGS. 3A and 4A, the surgeon will identify significant bone loss in proximal regions of the bone, e.g., extending down into the tibia and laterally away from the general longitudinal axis of the tibia in one or more directions, perhaps in an eccentric manner relative to the main tibial axis (e.g., as shown in FIG. 4A) indicating the need for an augment structure (e.g., a frustoconical augment body) that has a stem passage that is offset somewhat from the central longitudinal axis of the augment body. An example of such an augment structure is discussed above in relation to FIG. 2 where the trial cone 52 has a bore 70 that is offset from the central longitudinal axis of the right frustoconical member 52. Such a trial is generally suitable for the type of opening 66 shown in FIGS. 3A and 4A.

Figure 4B:
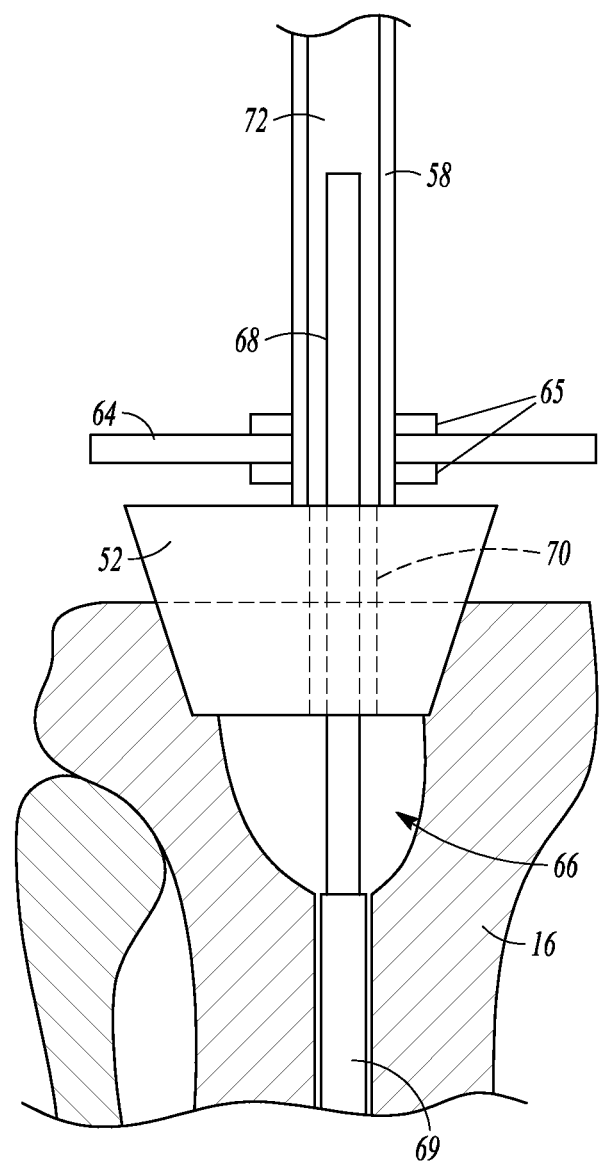

FIGS. 3B and 4B show the method after the trial cone 52 has been partially inserted into the opening 66 in the tibia 14. As shown best in FIG. 4B, in an example, the alignment rod 68 can axially align the trial cone 52 with respect to the tibia 14, for example by the trial cone 52 being placed over the alignment rod 68, such as by receiving the alignment rod 68 through the offset bore 70 in the trial cone 52. FIGS. 3B and 4B also show the handle 58 coupled with the trial cone 52. As best shown in FIG. 4B, in an example, the alignment rod 68 can fit within a hollow bore 72 within the handle 58. FIGS. 3B and 4B also show the alignment member 64 being placed onto the handle 58 (as in FIG. 3B) and with the alignment member 64 being coupled with the handle 58 (as in FIG. 4B). A surgeon or other medical practitioner can ensure that the alignment member 64 is properly aligned prior to broaching the tibia 16 with the broaching trial cone 52, for example, with respect to the tibia 16, or with respect to the femur 22 or a trial femoral component that has been coupled with the femur 22 (not shown).

Figure 4C:
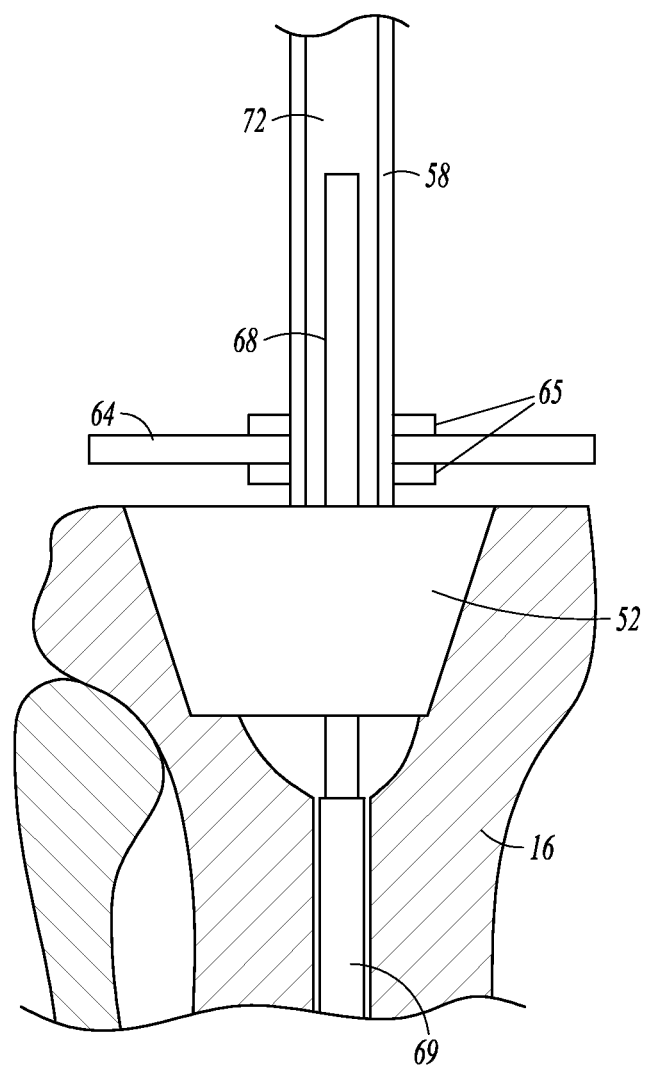

FIGS. 3C and 4C show the method after the trial cone 52 has broached the tibia 16. As shown in FIG. 4C, the trial cone 52 has been driven into the tibia 16 such that an upper surface of the trial cone 52 is substantially flush with a resected top surface of the tibia 16, although a flush alignment is not required. In some instances, for example, where a resection cut line occurs at some angle relative to the main longitudinal axis, only a portion a broaching member such as trial cone 52 will be flush with a resected top surface of the tibia, or no portion of the broaching member will be flush. FIG. 3C shows that the alignment member 64 was kept in substantially the same alignment with respect to the tibia 16 as it was before broaching (FIG. 3B). Because the alignment member 64 can be in a rotationally fixed relationship with respect to the trial cone 52, e.g., via the rotationally-fixed coupling between the alignment member 64 and the handle 58 and the rotationally-fixed coupling between the handle 58 and the trial cone 52, the continued alignment of the alignment member 64 during broaching also ensures continued alignment of the trial cone 52 during broaching.

Figure 4D:
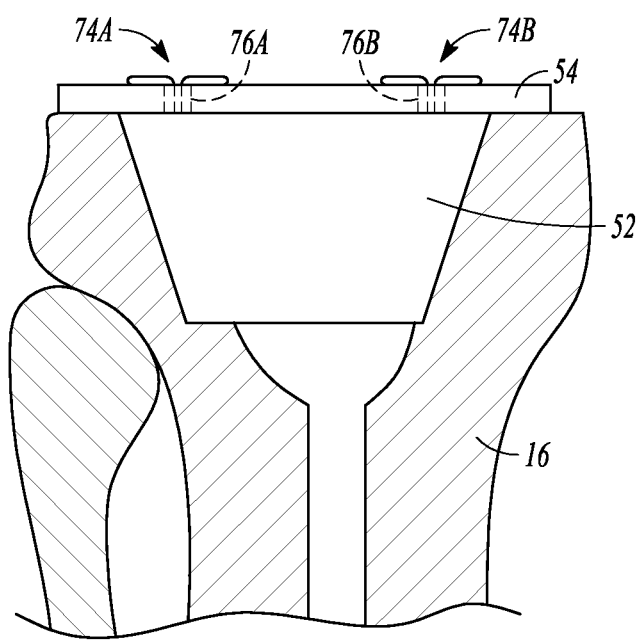

FIGS. 3D and 4D show the trial cone 52 after the handle 58 and the alignment member 64 have been decoupled from the trial cone 52. FIG. 3D shows the trial base plate 54 as it is being positioned with respect to the trial cone 52, while FIG. 4D shows the trial base plate 54 after it has been coupled with the trial cone 52. The coupling of the trial base plate 54 to the trial cone 52 can be achieved by any coupling mechanism, such as split pins 74A, 74B extending from the upper surface of the trial cone 52 for retention with respect to the trial base plate 54, for example, with a first split pin 74A passing through a first opening 76A in the trial base plate 54 for retention on a medial side of the trial base plate 54 and a second split pin 74B passing through a second opening 76B in the trial base plate 54 for retention on a lateral side of the trial base plate 54. Any suitable one- or multiple-piece coupling mechanism may be used to couple the trial cone 52 to the trial base plate 54. Examples include detents on one of the trial cone 52 or the trial base plate 54 that engage with a receiving structure, such as a depression, in the other of the trial cone 52 and the trial base plate 54.

In an example, the relative orientation or alignment of the trial cone 52 with respect to the trial base plate 54 is controlled to be substantially the same as the relative orientation or alignment of the trial cone 52 with respect to the alignment member 64 before the alignment member was decoupled from the trial cone 52. In an example, this alignment of the trial cone 52 with respect to the trial base plate 54 is provided by the attachment structure that couples the trial cone 52 and the trial base plate 54. For example, the attachment structure can comprise at least two attachment components on each of the trial base plate 54 and the trial cone 52, where coupling of the trial cone 52 to the trial base plate 54 can only be accomplished when the trial cone 52 and the trial base plate 54 are properly aligned or oriented with respect to each other so that the two or more attachment components on the trial cone 52 are aligned with the two or more attachment components on the trial base plate 54.

In the example where split pins 74A, 74B are used to couple the trial base plate 54 to the trial cone 52, at least two split pins 74A, 74B extending from the trial cone 52 and at least two receiving structures on the trial base plate 54, such as the openings 76A, 76B, (or vice versa) can be used, where the location of the split pins and the receiving structures are oriented so that the trial base plate 54 will be coupled to the trial cone 52 only if the trial base plate 54 is aligned correctly with respect to the trial cone 52. The location of the split pins 74A, 74B with respect to the trial cone 52 and the location of the openings 76A, 76B in the trial base plate 54 are selected so that when the split pins 74A, 74B are extended through the openings 76A, 76B, the trial base plate 54 will have substantially the same orientation or alignment with respect to the trial cone 52 as the alignment member 64 had with respect to the trial cone 52 before the alignment member 64 was decoupled from the trial cone 52.

In another example, not shown, alignment of the trial cone 52 with respect to the trial base plate 54 can be achieved by the use of at least one keyed structure on either the trial cone 52 or the trial base plate 54 that is received by a receiving structure on the other of the trial cone 52 and the trial base plate 54. For example, the keyed structure can comprise a stem or other projection having a selected cross-sectional shape projecting from the trial base plate 54 that is received by an opening in the trial cone 52 having substantially the same cross-sectional shape.

When coupled together, the trial cone 52 and the trial base plate 54 form a trial tibial component that simulates a permanent tibial component such as component 12 which incorporates a conical augment shaped similarly to the trial cone. A trial articulation component (not shown in FIG. 4D) that simulates the permanent articulation component 24 can be placed on the trial base plate 54 and a trial femoral component (not shown) can be inserted into the femur 22 of the patient. In an example, the trial femoral component can be located in the bone in much the same way as the trial tibial component (e.g., by providing a conical broaching trial that broaches into the femur 22, wherein the broaching can be achieved while using an alignment member that provides for the alignment of the broaching cone with respect to at least one of the femur 22, the tibia 16, or the trial tibial component, followed by coupling a trial condyle portion that simulates the condyle portion 36).

A surgeon or other medical practitioner can perform a trial reduction of the trial tibial component, the trial articulation component, and the trial femoral component to determine if the current configuration will be acceptable for the patient, e.g., will provide for an acceptable range of motion. If the current configuration is not acceptable, then the surgeon or other medical practitioner can alter the geometry of the trial tibial component, the trial articulation component, or the trial femoral component, for example by adding or removing spacer material that alters the position or orientation of one of the components with respect to another of the components.

Figure 5:
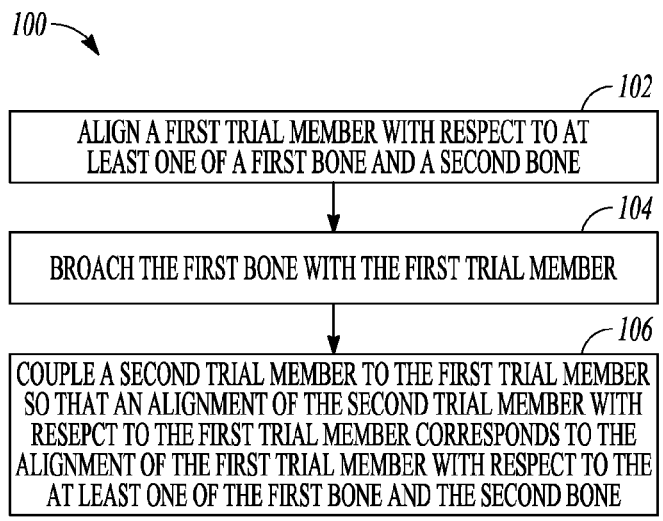
FIG. 5 is a flow diagram of an example method of installing a trial system into a bone of a patient.

FIG. 5 is a flow chart of an example method 100 of using a trial system, such as trial system 50 shown in FIG. 2. The example method 100 comprises a first step 102 which includes aligning a first trial member like trial cone 52 with respect to at least one of a first bone of the patient, such as the tibia 16, and a second bone of the patient, such as the femur 22; and a second step 104 that includes broaching the first bone of a patient, e.g., the tibia 16, with the first trial member to form a broach cavity in the first bone. The second step can comprise striking a handle like handle 58 coupled to the first trial member, for example, with an impactor tool such as a hammer or mallet in order to drive the first trial member into the first bone. In some embodiments, the alignment of the first step 102 is maintained substantially throughout the broaching of the second step 104.

Additionally, the method 100 shown in FIG. 5 can comprise a third step 106 that includes coupling a second trial member like trial base plate 54 to the first trial member. In an example, the coupling of the second trial member to the first trial member is such that an alignment of the second trial member with respect to the first trial member corresponds to the alignment of the first trial member with respect to the first bone.

Figure 6:
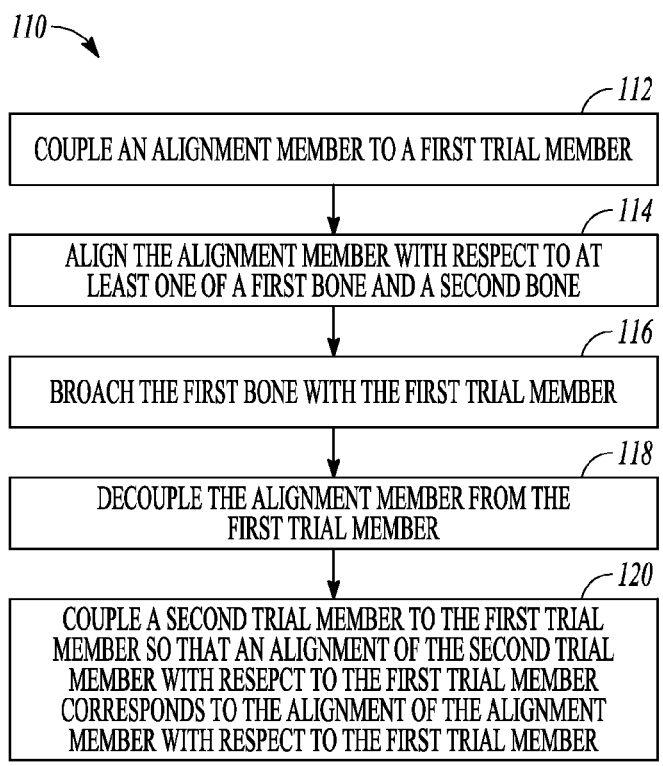
FIG. 6 is a flow diagram of another example method of installing a trial system into a bone of a patient.

FIG. 6 is a flow chart of another example method 110 of using a trial system, such as trial system 50. This method comprises a first step 112 that includes coupling an alignment member like alignment member 64 to a first trial member like trial cone 52. First step 112 can involve directly coupling the alignment member to the first trial member, or coupling both the first trial member and the alignment member to one or more intermediate structures such as a handle like handle 58. A second step 114 includes aligning the alignment member with respect to at least one of a first bone and a second bone. In an example, the first trial member and the alignment member are configured so that when they are coupled together, they are in a desired alignment with respect to each other. As described herein above, the alignment member can include indicia that assist a user, such as a surgeon or other medical practitioner, in aligning the alignment member in a selected alignment with respect to the at least one of the first bone and the second bone. For example, the alignment member may have a geometry that is substantially similar to the geometry of a second trial member like trial base plate 54 so that the user can align the alignment member in a position of the second trial member that would be acceptable, e.g., with respect to the first bone or the second bone.

Method 110 further comprises a third step 116 that includes broaching the first bone with the first trial member. A fourth step 118 includes decoupling the alignment member from the first trial member which can be performed either before are after the third step 116. A fifth step 120 includes coupling a second trial member like trial base plate 54 to the first trial member so that an alignment of the second trial member with respect to the first trial member corresponds to the alignment of the alignment member with respect to the first trial member. In an example, the fifth step 120 is performed after the third step 116 and also after the fourth step 118. In an example, the first trial member and the second trial member are configured such that when they are coupled together, the alignment of the second trial member with respect to the first trial member is substantially the same as the alignment of the alignment member had been with respect to the first trial member before the fourth step 118 is performed. The coupling in the fifth step 120 can be accomplished with any attachment structure that is suitable, such as the split pins 74A, 74B shown in FIG. 4D.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An orthopedic system comprising:
a first trial member capable of forming a broach cavity in a first bone of a patient, the first trial member having an outer surface comprising a surface feature for broaching the first bone;
a second trial member removeably coupleable to the first trial member in a fixed alignment with respect to the first trial member; and
an alignment member removeably coupleable in a fixed alignment with respect to the first trial member, the alignment member comprising indicia configured to provide for alignment of the alignment member with respect to at least one of the first bone of the patient and a second bone of the patient;
wherein the alignment of the second trial member with respect to the first trial member when coupled to the first trial member corresponds to the alignment of the alignment member with respect to the first trial member when coupled with the first trial member.

2. The orthopedic system of claim 1, wherein the first trial member and the alignment member are each configured so that the first trial member and the alignment member are in desired alignment with respect to each other when the alignment member is coupled to the first trial member.

3. The orthopedic system of claim 1, wherein the alignment member has a geometry that is substantially similar to a geometry of the second trial member.

4. The orthopedic system of claim 1, wherein the alignment of the second trial member with respect to the first trial member when coupled to the first trial member is substantially the same as the alignment of the alignment member with respect to the first trial member when coupled with the first trial member.

5. The orthopedic system of claim 1, comprising a handle removeably coupleable to at least one of the first trial member and the second trial member.

6. The orthopedic system of claim 5, wherein the alignment member is removeably coupleable to the handle.

7. The orthopedic system of claim 1, wherein the first trial member comprises a trial conical augment for inserting within a tibia of the patient and the second trial member comprises a trial base plate of a tibial component of an artificial knee implant trial.

8. An orthopedic system comprising:
a first trial member capable of forming a broach cavity in a first bone of a patient, the first trial member having an outer surface comprising a surface feature for broaching the first bone;
an alignment member for aligning the first trial member with respect to at least one of the first bone of the patient and a second bone of the patient; and
a second trial member removeably coupleable to the first trial member in a fixed alignment with respect to the first trial member;
wherein the fixed alignment of the second trial member with respect to the first trial member when coupled to the first trial member corresponds to the alignment of the alignment member with respect to the first trial member when coupled with the first trial member.

9. The orthopedic system of claim 8, wherein the first trial member and the alignment member are each configured so that the first trial member and the alignment member are in desired alignment with respect to each other when the alignment member is coupled to the first trial member.

10. The orthopedic system of claim 8, wherein the alignment member has a geometry that is substantially similar to a geometry of the second trial member.

11. The orthopedic system of claim 8, wherein the alignment of the second trial member with respect to the first trial member when coupled to the first trial member is substantially the same as the alignment of the alignment member with respect to the first trial member when coupled with the first trial member.

12. The orthopedic system of claim 8, comprising a handle removeably coupleable to at least one of the first trial member and the second trial member.

13. The orthopedic system of claim 12, wherein the alignment member is removeably coupleable to the handle.

14. The orthopedic system of claim 8, wherein the first trial member comprises a trial conical augment for inserting within a tibia of the patient and the second trial member comprises a trial base plate of a tibial component of an artificial knee implant trial.

15. A method comprising:
aligning a first trial member with respect to at least one of a first bone of a patient and a second bone of the patient;
broaching the first bone with the first trial member, the first trial member having an outer surface comprising a surface feature for broaching the first bone; and
coupling a second trial member to the first trial member so that an alignment of the second trial member with respect to the first trial member corresponds to the alignment of the first trial member with respect to the at least one of the first bone and the second bone.

16. The method of claim 15, wherein aligning the first member with respect to the at least one of the first bone and the second bone comprises coupling an alignment member to the first trial member and aligning the alignment member with respect to the at least one of the first bone and the second bone.

17. The method of claim 16, wherein the first trial member and the alignment member are each configured so that the first trial member and the alignment member are in desired alignment with respect to each other when the alignment member is coupled to the first trial member.

18. The method of claim 16, wherein the alignment member comprises indicia that assist a user in aligning the alignment member with respect to the at least one of the first bone and the second bone.

19. The method of claim 16, wherein the alignment member has a geometry that is substantially similar to a geometry of the second trial member.

20. The method of claim 16, comprising decoupling the alignment member from the first trial member before coupling the second trial member to the first trial member.

* * * * *